(12) United States Patent
Hamel et al.

(10) Patent No.: US 8,277,466 B2
(45) Date of Patent: Oct. 2, 2012

(54) ANASTOMOSIS DEVICE AND METHOD

(75) Inventors: Kory P. Hamel, Bloomington, MN (US); Vincent G. Copa, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 493 days.

(21) Appl. No.: 11/939,668

(22) Filed: Nov. 14, 2007

(65) Prior Publication Data
US 2008/0200935 A1    Aug. 21, 2008

Related U.S. Application Data

(60) Provisional application No. 60/865,750, filed on Nov. 14, 2006.

(51) Int. Cl.
*A61B 17/08* (2006.01)
(52) U.S. Cl. ....................................................... 606/153
(58) Field of Classification Search ................ 623/1.23, 623/1.36; 606/151, 153, 154, 155, 156; 604/544
See application file for complete search history.

(56) References Cited

U.S. PATENT DOCUMENTS

| | | | |
|---|---|---|---|
| 4,553,542 A * | 11/1985 | Schenck et al. | ........... 606/153 |
| 4,701,162 A | 10/1987 | Rosenberg | |
| 4,705,502 A | 11/1987 | Patel | |
| 4,792,330 A | 12/1988 | Lazarus | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 5,047,039 A | 9/1991 | Avant et al. | |
| 5,123,908 A | 6/1992 | Chen | |
| 5,152,772 A | 10/1992 | Sewell, Jr. | |
| 5,306,226 A | 4/1994 | Salama | |
| 5,540,701 A | 7/1996 | Sharkey et al. | |
| 5,545,171 A | 8/1996 | Sharkey et al. | |
| 5,695,504 A | 12/1997 | Gifford, III et al. | |
| 5,707,380 A | 1/1998 | Hinchliffe et al. | |
| 5,833,698 A | 11/1998 | Hinchliffe et al. | |
| 5,931,842 A | 8/1999 | Goldsteen et al. | |
| 5,964,791 A | 10/1999 | Bolmsjo | |
| 6,024,748 A | 2/2000 | Manzo et al. | |
| 6,119,045 A | 9/2000 | Bolmsjo | |
| 6,149,667 A | 11/2000 | Hovland et al. | |

(Continued)

FOREIGN PATENT DOCUMENTS
WO    WO 92/04869    4/1992

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Ryan Severson
*Assistant Examiner* — Jonathan W Miles
(74) *Attorney, Agent, or Firm* — Kimberly K. Baxter; Gregory L. Koeller

(57) ABSTRACT

An apparatus and method for using an anastomosis device to repair severed tissues resulting from a surgical medical procedure such as a radical prostatectomy, ilio-orthotopic neo-bladder construction, cystoprostatectomy, cystectomy, urethral anastomosis, or ureteral anastomosis.

3 Claims, 15 Drawing Sheets

U.S. PATENT DOCUMENTS

| | | |
|---|---|---|
| 6,193,734 B1 | 2/2001 | Bolduc et al. |
| 6,238,368 B1 | 5/2001 | Devonec |
| 6,254,570 B1 | 7/2001 | Rutner et al. |
| 6,299,598 B1 | 10/2001 | Bander |
| 6,302,605 B1 | 10/2001 | Goldsteen et al. |
| 6,391,039 B1 | 5/2002 | Nicholas et al. |
| 6,416,545 B1 | 7/2002 | Mikus et al. |
| 6,440,146 B2 | 8/2002 | Nicholas et al. |
| 6,447,533 B1 | 9/2002 | Adams |
| 6,461,367 B1 | 10/2002 | Kirsch et al. |
| 6,485,496 B1 | 11/2002 | Suyker et al. |
| 6,494,908 B1 | 12/2002 | Huxel et al. |
| 6,520,974 B2 | 2/2003 | Tanner et al. |
| 6,530,932 B1 | 3/2003 | Swayze et al. |
| 6,562,024 B2 | 5/2003 | Alvarez de Toledo et al. |
| 6,565,579 B2 | 5/2003 | Kirsch et al. |
| 6,599,311 B1 | 7/2003 | Biggs et al. |
| 6,602,243 B2 | 8/2003 | Noda |
| 6,695,832 B2 | 2/2004 | Schon et al. |
| 6,702,825 B2 | 3/2004 | Frazier et al. |
| 6,719,709 B2 | 4/2004 | Whalen et al. |
| 6,719,749 B1 | 4/2004 | Schweikert et al. |
| 6,726,697 B2 | 4/2004 | Nicholas et al. |
| 6,740,098 B2 | 5/2004 | Abrams et al. |
| 6,746,456 B2 | 6/2004 | Xiao |
| 6,746,472 B2 | 6/2004 | Frazier et al. |
| 6,821,283 B2 | 11/2004 | Barzell et al. |
| 2001/0049492 A1 | 12/2001 | Frazier et al. |
| 2002/0002363 A1 | 1/2002 | Urakawa et al. |
| 2002/0087176 A1 | 7/2002 | Greenhalgh |
| 2003/0069629 A1 | 4/2003 | Jadhav et al. |
| 2003/0208183 A1 | 11/2003 | Whalen et al. |
| 2003/0229364 A1 | 12/2003 | Seiba |
| 2004/0078047 A1 | 4/2004 | Nicholas et al. |
| 2004/0087995 A1 | 5/2004 | Copa et al. |
| 2005/0070938 A1 | 3/2005 | Copa et al. |
| 2005/0131431 A1 | 6/2005 | Copa et al. |
| 2005/0251155 A1 | 11/2005 | Orban, III |
| 2006/0200178 A1 | 9/2006 | Hamel et al. |
| 2006/0264985 A1 | 11/2006 | Copa et al. |
| 2006/0276811 A1 | 12/2006 | Copa et al. |
| 2007/0219584 A1 | 9/2007 | Copa et al. |

FOREIGN PATENT DOCUMENTS

| | | |
|---|---|---|
| WO | WO 96/07447 | 3/1996 |
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |
| WO | WO 2007/013070 | 2/2007 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

Hruby, G.W., "Comparison of a Novel Tissue Apposing Device and Standard Anastomotic Technique for Vesicourethral Anastomses," Journal of Endourology, vol. 20, Supplement 1 VP12-02, p. A69 (abstract) Aug. 2006.

Hruby, G.W., "Comparison of a Novel Tissue Apposing Device and Standard Anastomotic Technique for Vesicourethral Anastomses," Journal of Urology, vol. 175, No. 4, p. 347, Apr. 2006.

* cited by examiner

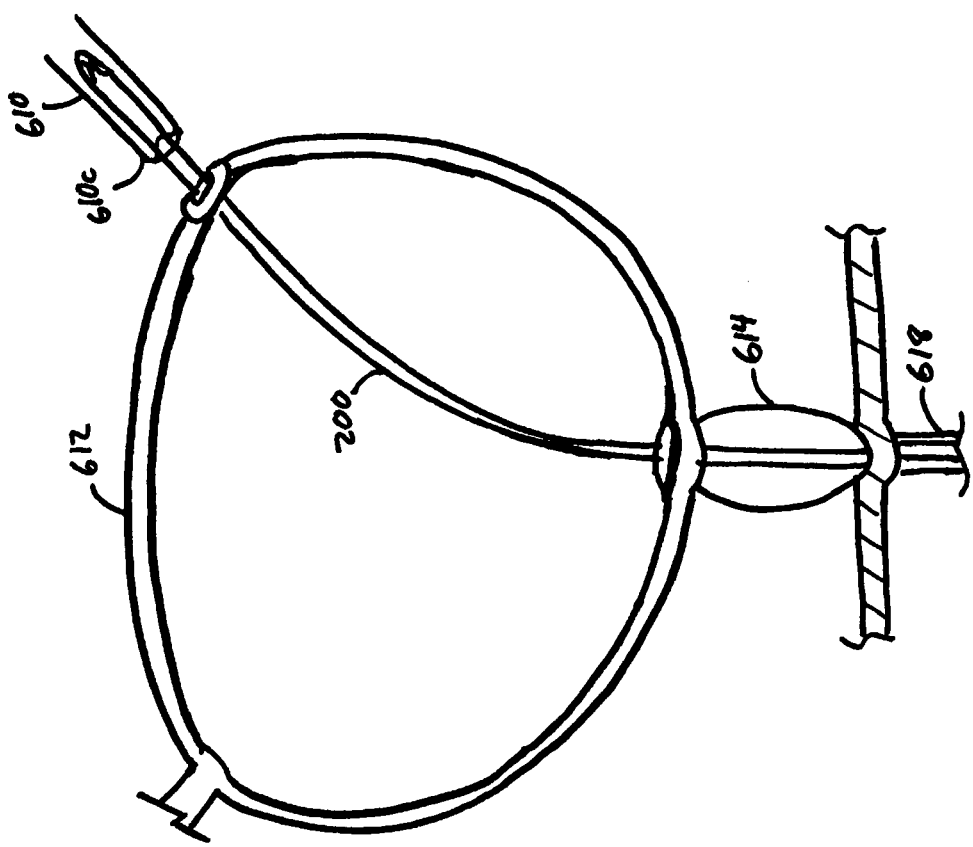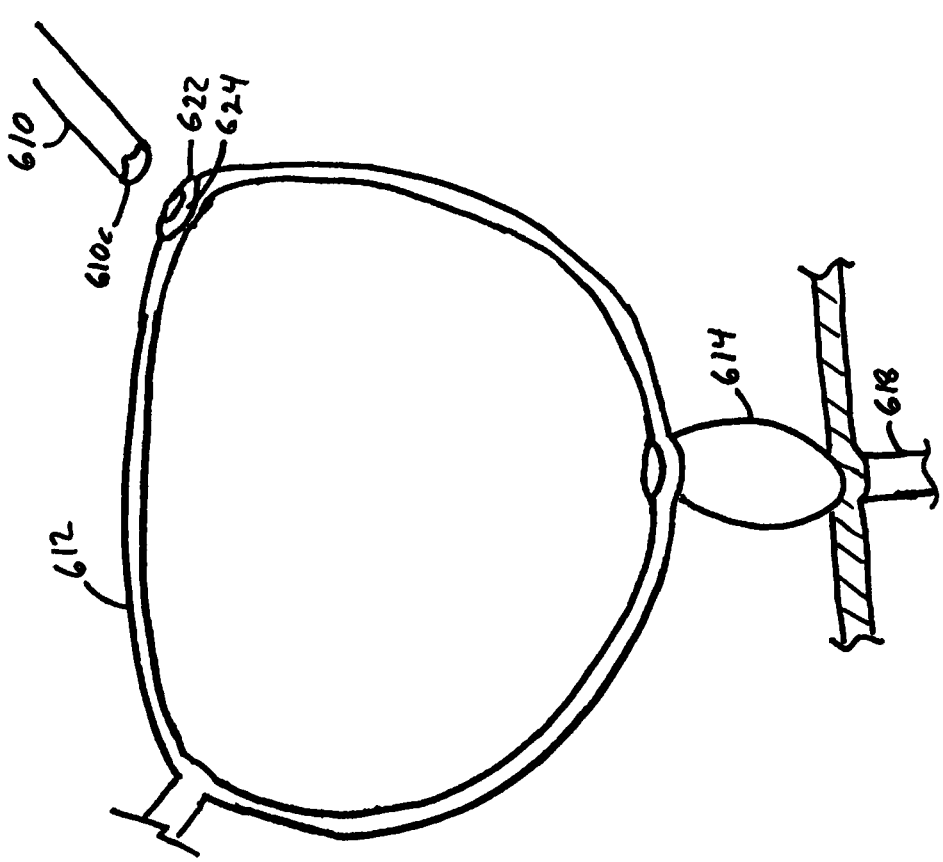

ANASTOMOSIS DEVICE AND METHOD

PRIORITY CLAIM

The present application claims the benefit of U.S. Provisional Application No. 60/865,750, filed Nov. 14, 2006, and entitled, "ANASTOMOSIS DEVICE APPLICATIONS, which is herein incorporated reference in its entirety.

FIELD OF THE INVENTION

The present application relates generally to anastomosis devices and related methods of using said anastomosis devices to perform anastomosis procedures. More particularly, the present application relates to an anastomosis device utilizing a plurality of inflation balloons and a plurality or retention features to conduct anastomosis procedures such as radical prostatectomy, ilio-orthotopic neobladder construction, cystoprostatectomy, cystectomy, urethral anastomosis, ureteral anastomosis, and other similar procedures.

BACKGROUND OF THE INVENTION

Conventionally, a surgeon may execute delicate suturing operations with tiny, fine needles to reconnect severed body lumens. However, installation of sutures with a needle to connect severed tissues can be a difficult and technique-sensitive task. Many factors can make the task difficult, including small amounts of tissue to work with (e.g., at the urethral stump and at a bladder neck), and proximity to sensitive tissues such as ureters at a bladder and a proximal nerve bundle and sphincter at a urethral stump. These factors result in complicated and delicate suturing procedures that, if not performed properly, can result in complications such as leakage, difficulty in healing or failure to heal, or specific conditions such as incontinence or impotence.

To reduce the risks involved in conventional suturing procedures, anastomosis devices have been developed that include a drainage feature and tissue approximating structure that allow for reconnection of tissues without using traditional sutures. Commercially, a representative anastomosis device can include those available from American Medical Systems of Minnetonka, Minn., which are further described in United States Patent Publications 2004/0087995, 2005/0070938, 2005/0131431 2006/0200178, 2006/0264985, 2006/0276811 and 2007/0219584, all of which are incorporated herein by reference in their entireties. These anastomosis devices advantageously use tissue approximating structures to reconnect severed tissues during anastomosis procedures. The anastomosis device reduce the risks during the surgical procedure and also provide a significant reduction in the amount of time required to perform certain anastomosis procedures. Because the anastomosis device will typically be surgically positioned within the patient for a significant period of time (e.g., while the healing process takes place), there is a need for the device to be sufficiently strong and flexible to accommodate the various stresses to which the device may be subjected while positioned within the patient.

Anastomosis procedures are generally performed to connect or reconnect certain body tissues, typically in the form of tubular structures as part of a surgical procedure. Typically, these tissues define a body lumen such as, for example, a blood vessel, intestinal, digestive or urinary tissue that has been severed and requires reconnection as part of a successful treatment.

One representative anastomosis procedure can include a radical prostatectomy procedure in which, a surgeon removes all or most of a patient's prostate. The procedure generally leaves a severed urethral stump and a severed bladder neck, which must be reconnected so as to restore proper urinary functions. Through the use of a combination of retention features including an inflation balloon and a plurality of tissue approximating structures, the urethral stump and bladder neck can be aligned and retained in contact throughout a healing period for the tissue. While the urethral stump and bladder neck are forcibly held in approximation during healing, the anastomosis device provides a drainage lumen allowing bodily fluids and other materials to pass through the drainage lumen during the healing period.

While the aforementioned anastomosis device effectively reconnects tissue during certain surgical procedures, it would be advantageous to provide an anastomosis device providing treatment options for additional anastomosis procedures and to improve upon present designs and methods to enhance the functionality, reliability and safety associated with use of anastomosis devices.

SUMMARY OF THE INVENTION

The present invention relates to methods of using anastomosis devices in applications for medical procedures including radical prostatectomy, ilio-orthotopic neobladder construction, cystoprostatectomy, cystectomy, urethral anastomosis, ureteral anastomosis, as well as other procedures where tissue structures require approximation and fluid transfer across a junction being repaired.

In one aspect, the invention relates to an embodiment of an anastomosis device for performing a variety of anastomosis procedures. The anastomosis device generally comprises an elongate body having a central lumen extending between a distal end and a proximal end. At the distal end, a drainage aperture is fluidly connected to a drainage lumen within the central lumen. The elongate body includes a plurality of inflation balloons including a distal inflation balloon, a medial inflation balloon and a proximal inflation balloon, wherein each balloon is individually connected to an inflation lumen within the central lumen. The elongate body further includes a distalmost pair of retention members positioned between the distal inflation balloon and the medial inflation balloon and a proximalmost pair of retention members positioned between the medial inflation balloon and the proximal inflation balloon. In some embodiments, the retention members comprise extendible tines. The distalmost pair of retention members can comprise a first set of tine members and a second set of tine members, wherein the first and second sets of tine members are independently deployable while the proximalmost pair of retention members comprises a third set of tine members and a fourth set of tine members, wherein the third and fourth sets of tine members are independently deployable. The anastomosis device is suited for use in a wide variety of anastomosis procedures including a radical prostatectomy procedure, a urethral anastomosis procedure, a cystectomy procedure, a cystoprostatectomy procedure or an ilio-orthotopic neobladder procedure.

In another aspect, the invention is directed to a method for performing a ureter-to-ureter anastomosis procedure. The method can comprise providing an anastomosis device including a distalmost pair of tines and a medial inflation balloon. A distal end of the anastomosis device can be advanced through a urinary tract and into a severed ureteral member such that a first tine set is positioned within a distal severed portion and a second tine set is positioned within a proximal severed portion. Once positioned, the first tine set can be extended to grasp the distal severed portion. Next, a medial inflation balloon is inflated within a bladder such that the medial inflation balloon is proximate the proximal severed portion. With the medial inflation balloon inflated, the bladder can be pushed on to direct the proximal severed portion into contact with the distal severed portion. The second tine set can then be extended to grasp the proximal severed portion and retain the proximal severed portion and the distal severed portion in approximation during a healing period. With the anastomosis device positioned as such, fluid in the distal severed portion can be drained through a drainage aperture at the distal end of the anastomosis device.

In another aspect, the invention is directed to a method for performing a ureter-to-bladder anastomosis procedure. The method initially comprises providing an anastomosis device including a distalmost pair of tines and a medial inflation balloon. The anastomosis device is advanced through the urinary tract such that a distal end of the anastomosis device is positioned within a severed ureteral member such that a first tine set is positioned within a distal severed portion and a second tine set is positioned within a bladder neck. The first tine set can then be extended to grasp the distal severed portion. With the distal severed portion retained, the medial inflation balloon can be inflated within the bladder such that the medial inflation balloon is proximate the bladder neck. Utilizing the inflated medial inflation balloon, the bladder can be pushed to direct the bladder neck into contact with the distal severed portion. The second tine set can then be extended to grasp the bladder neck and retain the bladder neck and the distal severed portion in approximation during a healing period. With the anastomosis device positioned as such, fluid in the severed ureteral member can be drained through a drainage aperture at the distal end of the anastomosis device.

In yet another aspect, the invention is directed to a method for performing a bladder replacement procedure such as a cystectomy procedure, a cystoprostatectomy procedure or an ilio-orthotopic neobladder procedure. Generally the method can comprise providing an anastomosis device having a distalmost pair of tines, a proximalmost pair of tines, a medial inflation balloon and a proximal inflation balloon. A distal end of the anastomosis device can be advanced through a urinary tract and into a severed ureteral member such that a first tine set is positioned within a distal severed portion and a second tine set is positioned within a ureteral bladder neck. The first tine set can then be extended to grasp the distal severed portion. With the distal severed portion retained, the medial inflation balloon can be inflated within the bladder such that the medial inflation balloon is proximate the ureteral bladder neck. Using the inflated medial inflation balloon, the bladder can be pushed on to direct the ureteral bladder neck into contact with the distal severed portion. The second tine set can then be deployed to grasp the ureteral bladder neck and retain the ureteral bladder neck and the distal severed portion in approximation. Next, a third tine set within the bladder can be extended to grasp a urethral bladder neck. A proximal inflation balloon within the bladder scan then be inflated such that the inflated proximal inflation balloon is proximate the urethral bladder neck. Using the inflated proximal inflation balloon, the bladder can be pulled on to direct the urethral bladder neck into contact with a severed urethral member. Finally, a fourth tine set can be deployed within the severed urethral member to grasp the severed urethral member and retain the severed urethral member and the urethral bladder neck in approximation during a healing period. With the anastomosis device positioned as such, fluid in the severed ureteral member can be drained through a drainage aperture at the distal end of the anastomosis device.

The above summary of the invention is not intended to describe each illustrated embodiment or every implementation of the present invention. The Figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 7a is a partial cross-sectional view of the anastomosis device of FIG. 5 performing a bladder-to-ureter repair procedure.

FIG. 7b is a partial cross-sectional view of the anastomosis device of FIG. 5 performing a bladder-to-ureter repair procedure.

Figure 1:
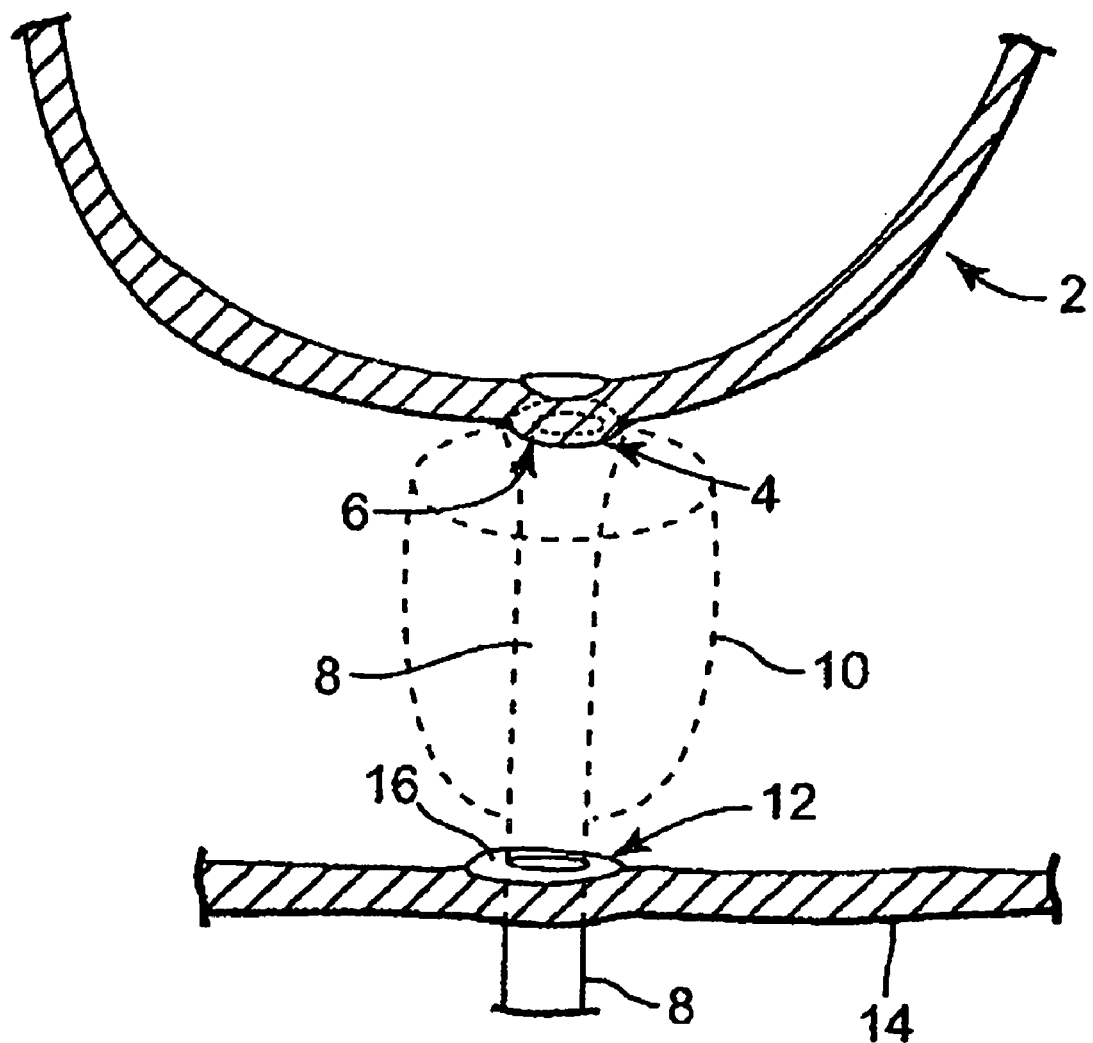
FIG. 1 is a partial cross-sectional view of internal body organs and illustrating general aspects of radical prostate removal of the prior art.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

According to specific embodiments and methods of the present invention, an anastomosis device includes tissue approximating structure that can be used to place or hold a cut or severed tissue or tissue surface in close approximation for healing while allowing drainage though a drainage lumen. The apparatus and methods disclosed in the embodiments of this application relate to surgical procedures including radical prostatectomy, urethral anastomosis, ureteral anastomosis, ureteral anastomosis, cycstectomy, cystoprostatectomy, ilio-orthotopic neobladder construction, and others which require approximation structures for tissue and fluid transfer across approximated junctions.

Figure 2:
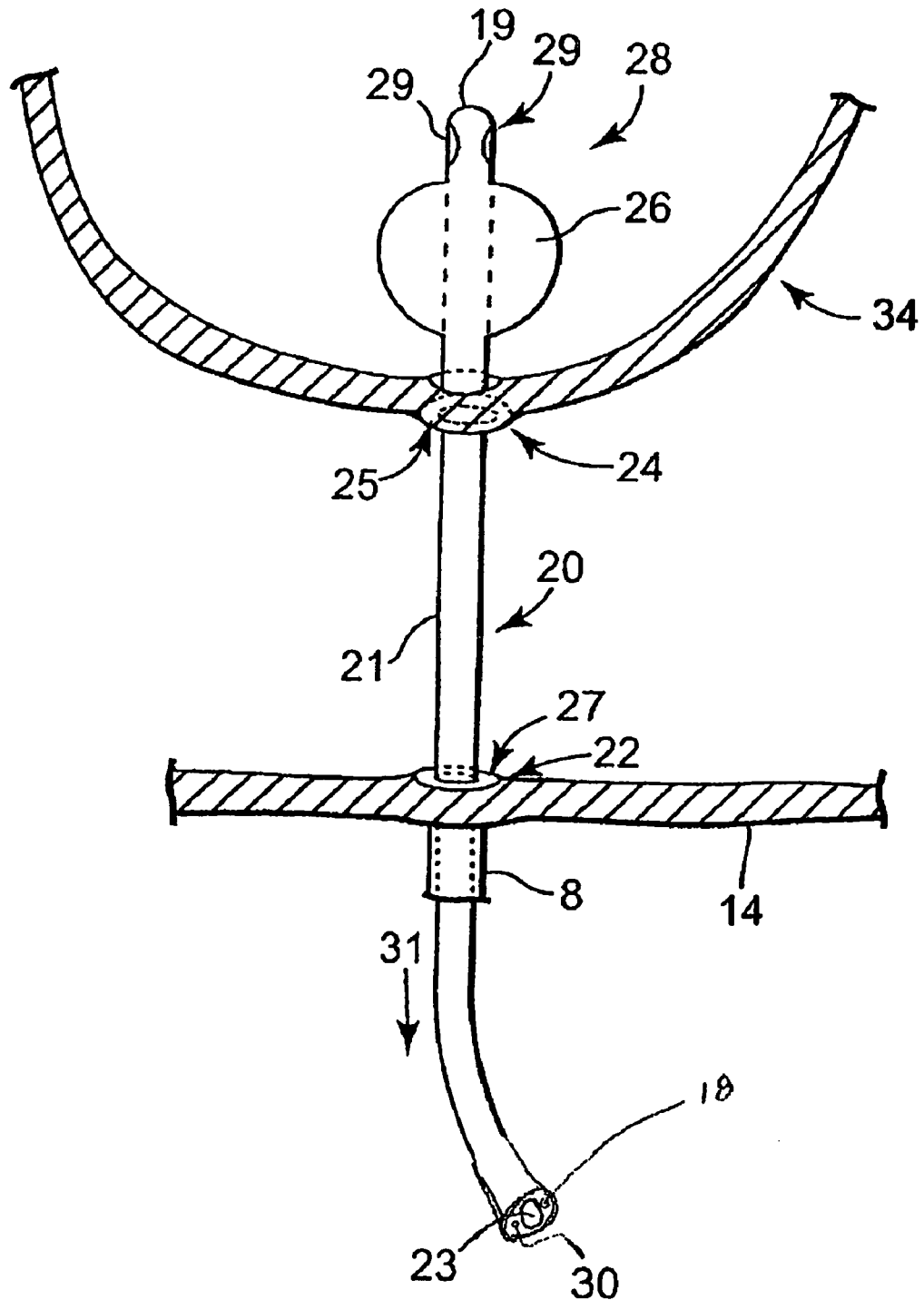
FIG. 2 is a partial cross-sectional view of an anastomosis procedure utilizing an embodiment of an anastomosis device of the prior art in a radical prostate removal and repair procedure.
Figure 3:
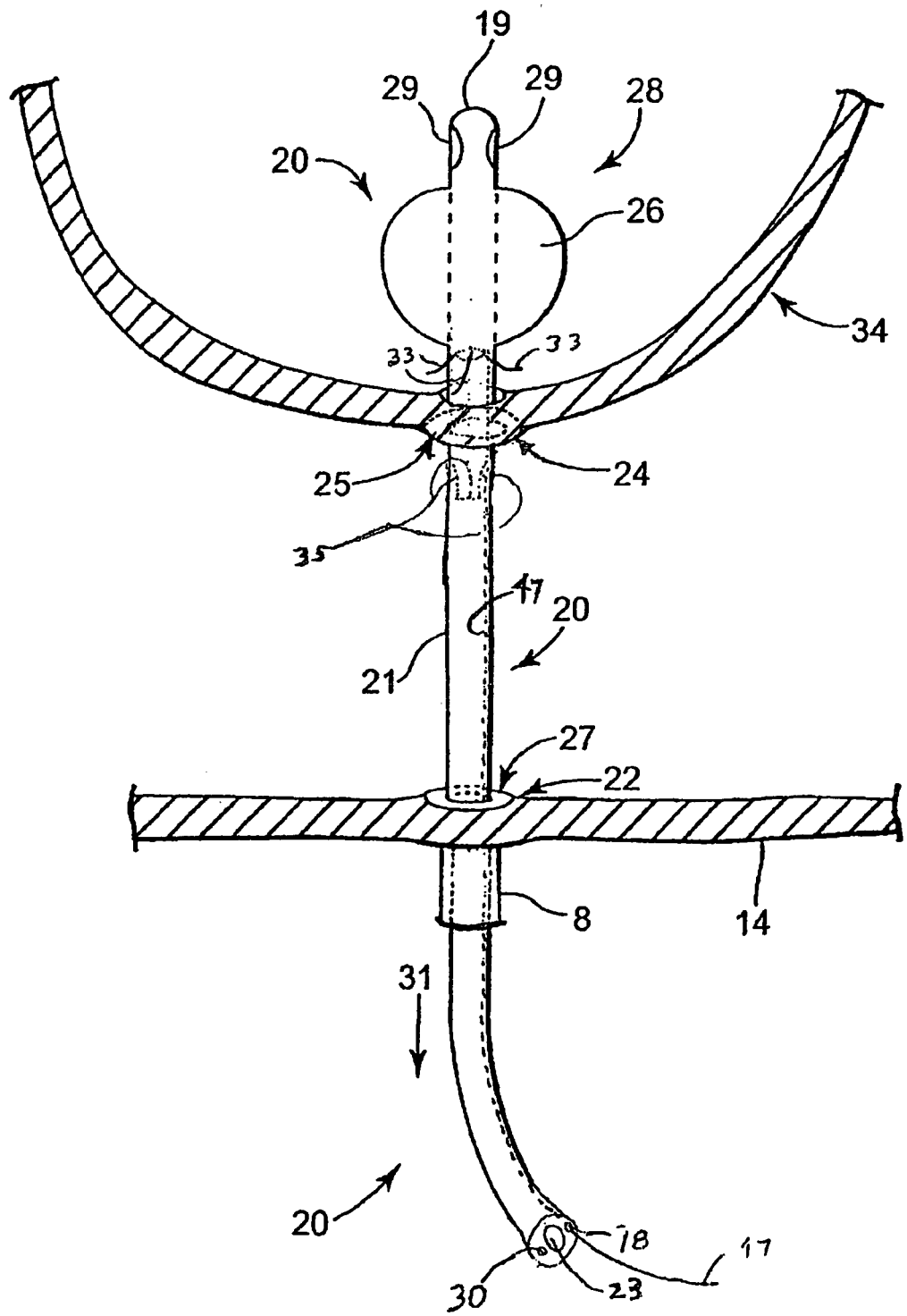
FIG. 3 is a partial cross-sectional view of an anastomosis procedure utilizing an embodiment of an anastomosis device of the prior art in a radical prostate removal and repair procedure.
Figure 3A:
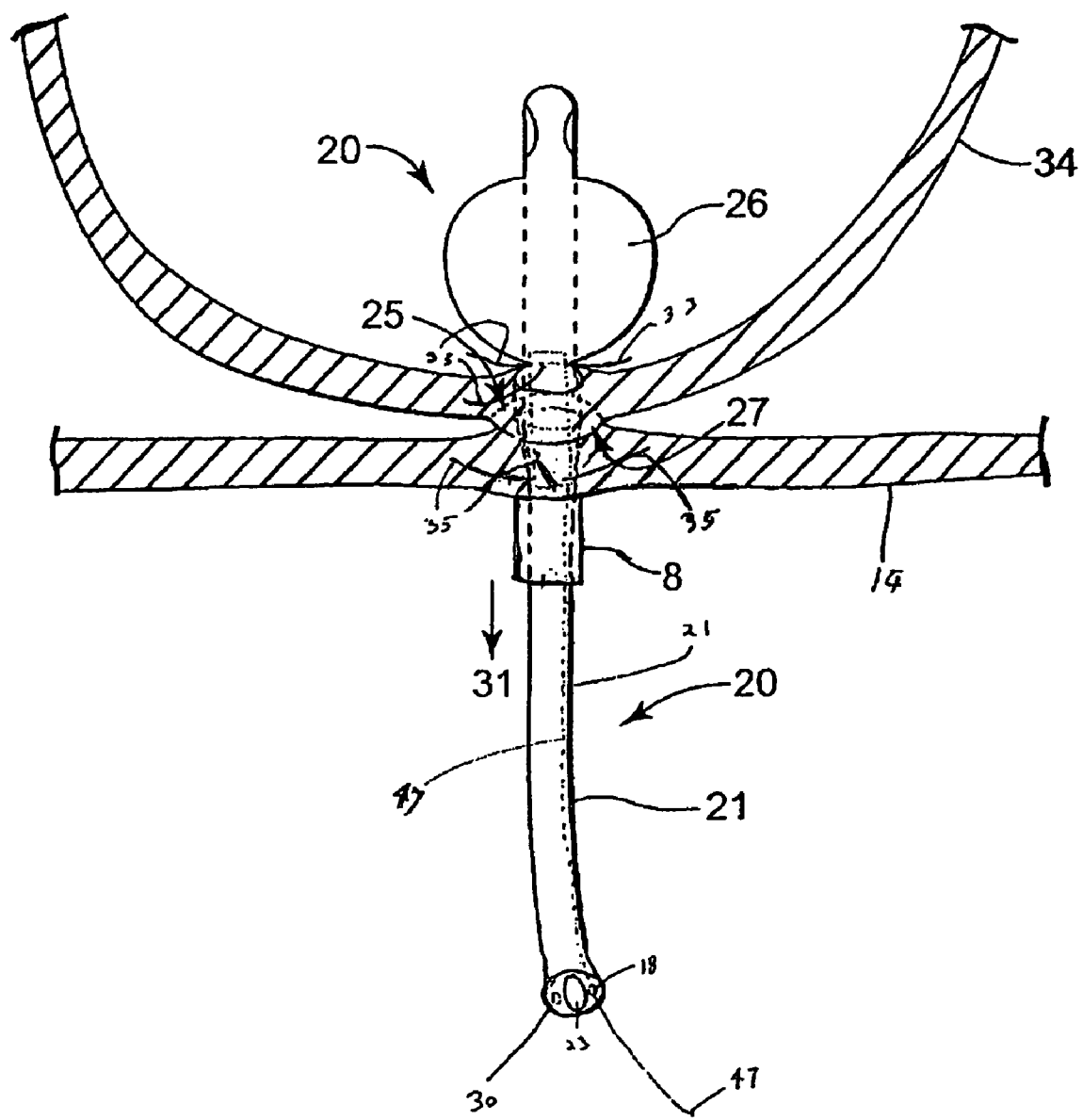
FIG. 3a is a partial cross-sectional view of an anastomosis procedure utilizing the anastomosis device of FIG. 3 in a radical prostate removal and repair procedure.
Figure 4:
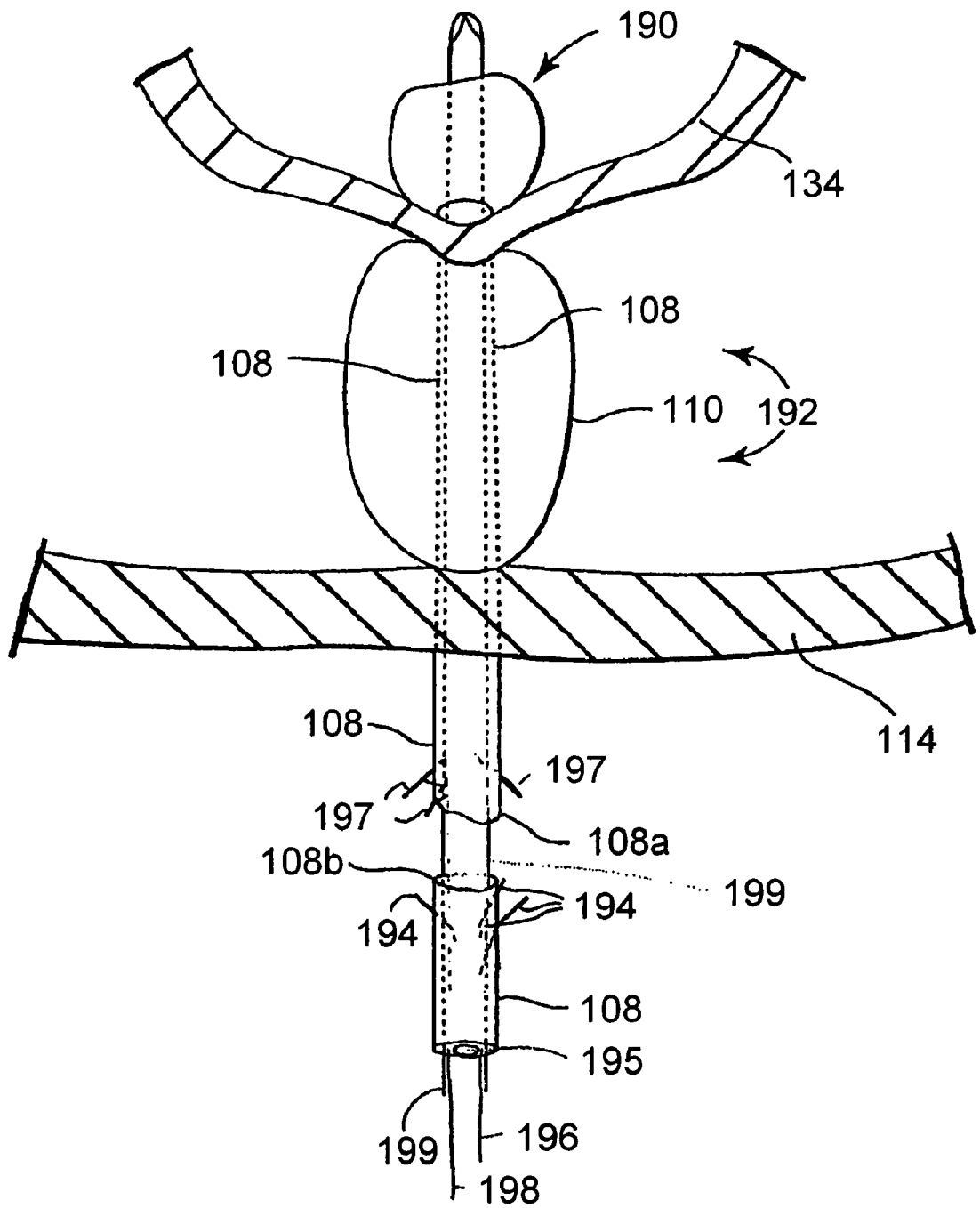
FIG. 4 is a partial cross-sectional view of an embodiment of an anastomosis device of the prior art used for securing two portions of a severed urethra.
Figure 4A:
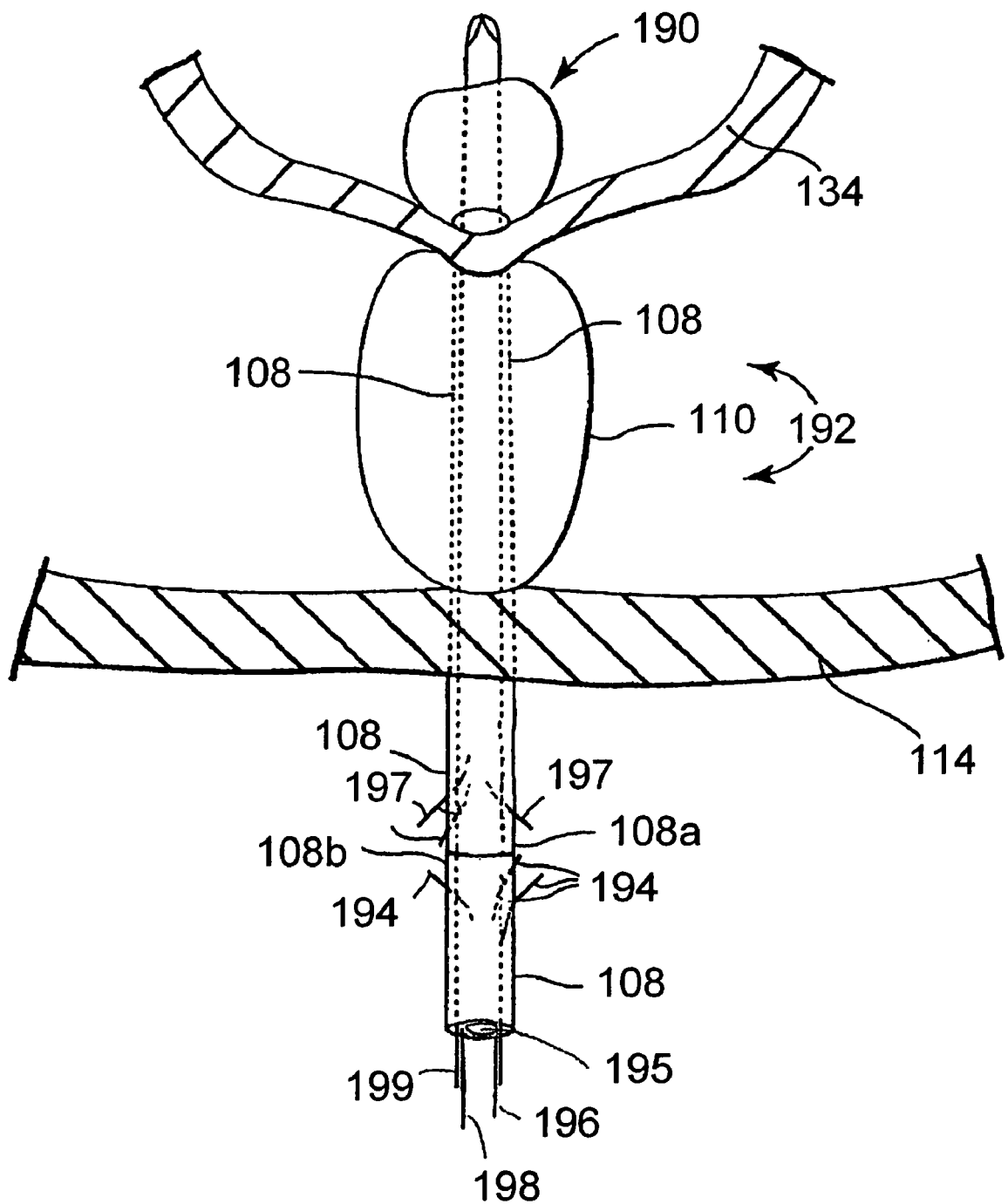
FIG. 4a is a partial cross-sectional view of the anastomosis device of FIG. 4 used for securing two portions of a severed urethra.

To better understand the advantages of the anastomosis device and related anastomosis procedures of the present invention, similar procedures using prior art anastomosis devises are illustrated and described in FIGS. 1-3a related to a radial prostatectomy procedure and in FIGS. 4 and 4a related to ureteral anastomosis procedures.

In a radical prostatectomy procedure, a surgeon removes all or most of a patient's prostate. The procedure generally leaves a severed urethral stump and a severed bladder neck, which must be reconnected so as to restore proper urinary functions.

Referring to FIG. 1, a radical prostatectomy procedure includes removal of the prostate 10 (indicated in dashes) and urethra 8 (also in dashes), leaving bladder 2 with bladder neck 4 having a severed tissue surface 6 at one end of removed urethra 8, and a urethral stump 12 extending from perineal floor 14, with urethral stump 12 having severed tissue surface 16 opposing the severed surface 6 of bladder neck 4.

Figure 2A:
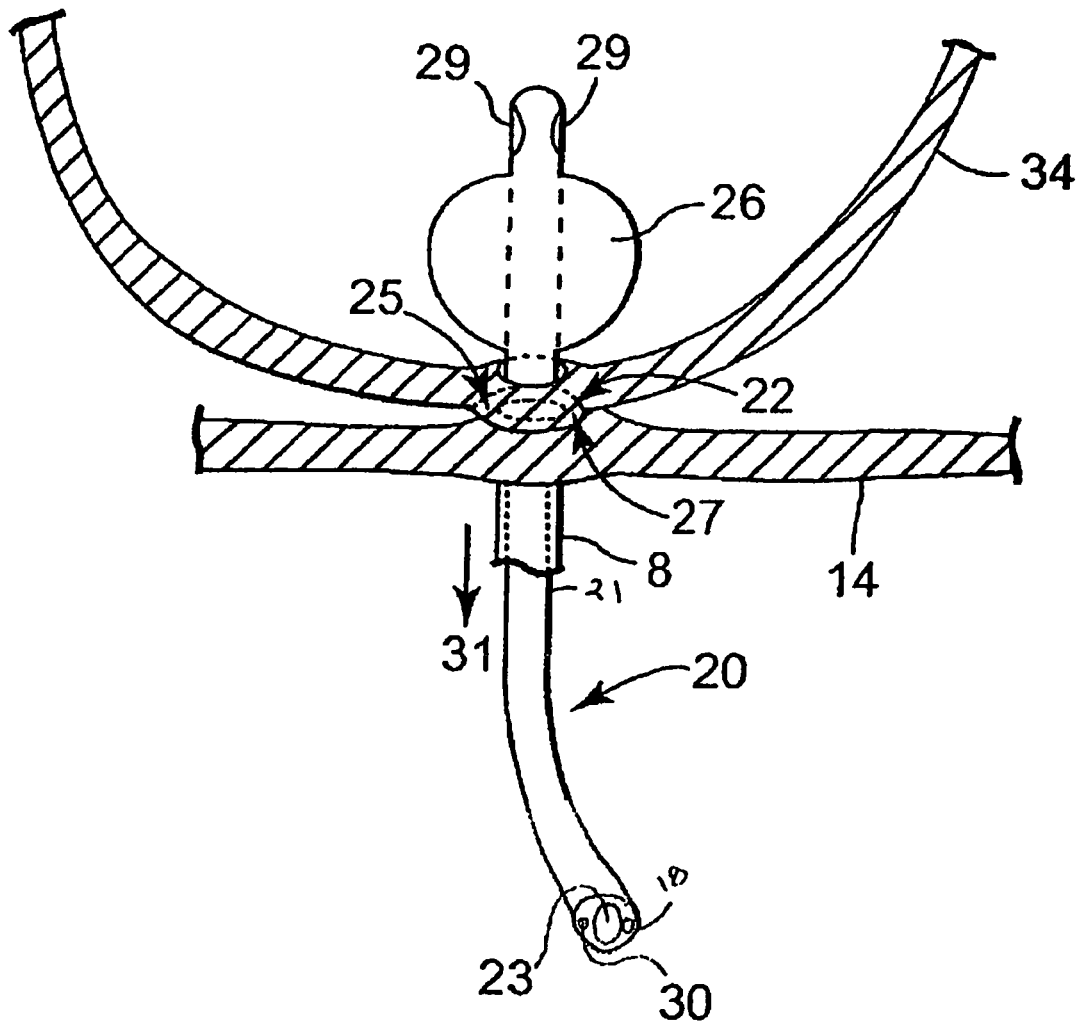
FIG. 2a is a partial cross-sectional view of an anastomosis procedure utilizing the anastomosis device of FIG. 2 in a radical prostate removal and repair procedure.

According to certain embodiments, an anastomosis device can comprise a balloon located at the distal end of the device, for being positioned inside of the bladder during use. FIGS. 2 and 2a illustrate such an embodiment of an anastomosis device, installed for use within urethra 8 and bladder 34 following removal of a prostate (not shown).

Referring to FIG. 2, a prostate has been removed to leave a severed urethral stump 22 and opposing severed bladder neck 24. Anastomosis device 20 is installed through urethral stump 22 and bladder neck 24. The device 20 comprises an elongate body 21 and balloon 26 located at the distal end 28 of the device. The device 20 further includes drainage lumen 23 in communication with drainage apertures 29, located between the tip 19 of the distal end of the device 20 and balloon 26. Balloon 26 is inflated, after insertion into the bladder 34, by a flow of fluid through inflation lumen 30. Traction, as shown by arrow 31, can then be applied through the length of device 20. Referring to FIG. 2a, balloon 26 can be placed against the interior of the bladder 34 with the severed bladder neck tissue 25 in contact with severed urethral stump 22. The surface of severed bladder neck tissue 25 can be aligned with the surface 27 of severed urethral stump 22, around and along the axis of the elongate body 21, provided that no gap exists between the surfaces 25 and 27 of the respective severed tissues.

The device 20 utilized in FIGS. 2 and 2a can includes tissue approximating structure aw will now be described but which are not illustrated for purposes of clarity in the figures. FIGS. 3 and 3a show the configurations of FIGS. 2 and 2a, respectively, with the inclusion of illustrated tissue approximation structure. As an example, FIG. 3 shows tissue approximating structure located along the length of the elongate body 21, at a location that will place the tissue approximating structure near the urethral stump 22 or the perineal floor 14. Such tissue approximating structure may include one or more sets of elongate metal tines. FIG. 3 shows two sets of tines, proximal tines 35 and distal tines 33. Proximal tines 35 are in a retracted position, and distal tines 33 are shown in an extended position. Actuating mechanisms, in the form of wires or shafts, are illustrated as a single dashed line 47 extending from the tissue approximating structures to the proximal end of the device, through actuating lumen 18. Proximal tines 35 cay extend from the elongate body 21 at a position (when installed, with the bladder drawn down to the perineal floor) below or proximal to the urethral stump 22 or perineal floor. Distal tines 33 can extend from body 21 at a location within bladder 34. Thus, in combination, extended distal tines 33 and extended proximal tines 35 can work together to maintain contact between urethral stump tissue 27 and bladder neck 24.

Referring again to FIG. 3, the prostate (not shown) has been removed to leave a severed urethral stump tissue 22 and opposing severed bladder neck 24. Anastomosis device 20 is installed through urethra 8, urethral stump 22, and bladder neck 24. The device 20 comprises balloon 26 located at distal end 28 of the device. The device also includes drainage lumen 23 in communication with drainage apertures 29. Balloon 26 is inflated and traction 31 is applied through the length of device 20 to cause distal tines 33 and balloon 26 to contact the inside of bladder 34 (see FIG. 3a) while severed bladder neck tissue 25 contacts severed urethral stump tissue 27. As shown in FIG. 3a, the surface 25 of the severed bladder neck can be aligned with the surface 27 of the severed urethral stump, around and along the axis of device 20. Also shown in FIG. 3a are proximal tines 35 extended from elongated body 21 to contact and optionally penetrate into perineal floor 14 (optionally contacting or penetrating tissue below the perineal floor 14 such as the bulbar urethra 8). Distal tines 33 extend from body 21, into bladder 34, to contact an interior surface of bladder 34. Severed urethral stump tissue 27 contacts severed surface 25 of the bladder neck to allow healing and reconnection of the two severed tissue surfaces.

The distal end of the anastomosis device 20 can optionally be partially installed during the prostatectomy procedure, e.g., up to the perineal floor, or may be installed to that point afterward. Following removal of the prostate, the distal end of the device 20 is passed through the urethral stump and then through the bladder neck. From there, the technique can include inflating the balloon 26 inside of the bladder, and using tissue approximating structure to hold the severed tissue surfaces of the urethral stump and the bladder neck into contact for healing. A preferred step can also be to close the bladder neck to a desired size via a purse-string suture.

FIG. 4 illustrates the use of an anastomosis device 190 in a urethral anastomosis procedure below the perineal floor. FIG. 4 illustrates device 190 having distal end 192 installed through perineal floor 114 and into bladder 134, through urethra 108 which passes through prostate 110. This procedure does not include removal of the prostate, but instead relates to severing and re-attaching urethra 108 at a point below perineal wall 114, e.g., re-attaching severed urethra portions 108a and 108b. As illustrated in FIG. 4a, tines 194 and 197 can be used to hold surfaces of severed urethra portions 108a and 108b together for healing. Specifically, proximal tines 194 and distal tines 197 are independently movable by actuating mechanisms 196 and 198, respectively, to retract or extend through elongate body 199. When installed, tines 194 and 197 are located along the body 199 at a location that allows each set of tines to contact a severed urethra tissue portion.

FIG. 4a illustrates the extended distal and proximal sets of tines 197 and 194 extending into opposing portions of severed urethra 108 and holding the severed tissue portions 108a and 108b in contact for healing. The installed device 190 also includes a balloon in bladder 134 and an open drainage lumen that function together to cause urine to collect in the bladder and drain from the bladder through open central drainage lumen 195. Thus, the illustrated device 190 can be left installed, including the tissue approximating structure, during the healing period. The open drainage lumen allows passage of bodily materials without clogging.

Figure 5:
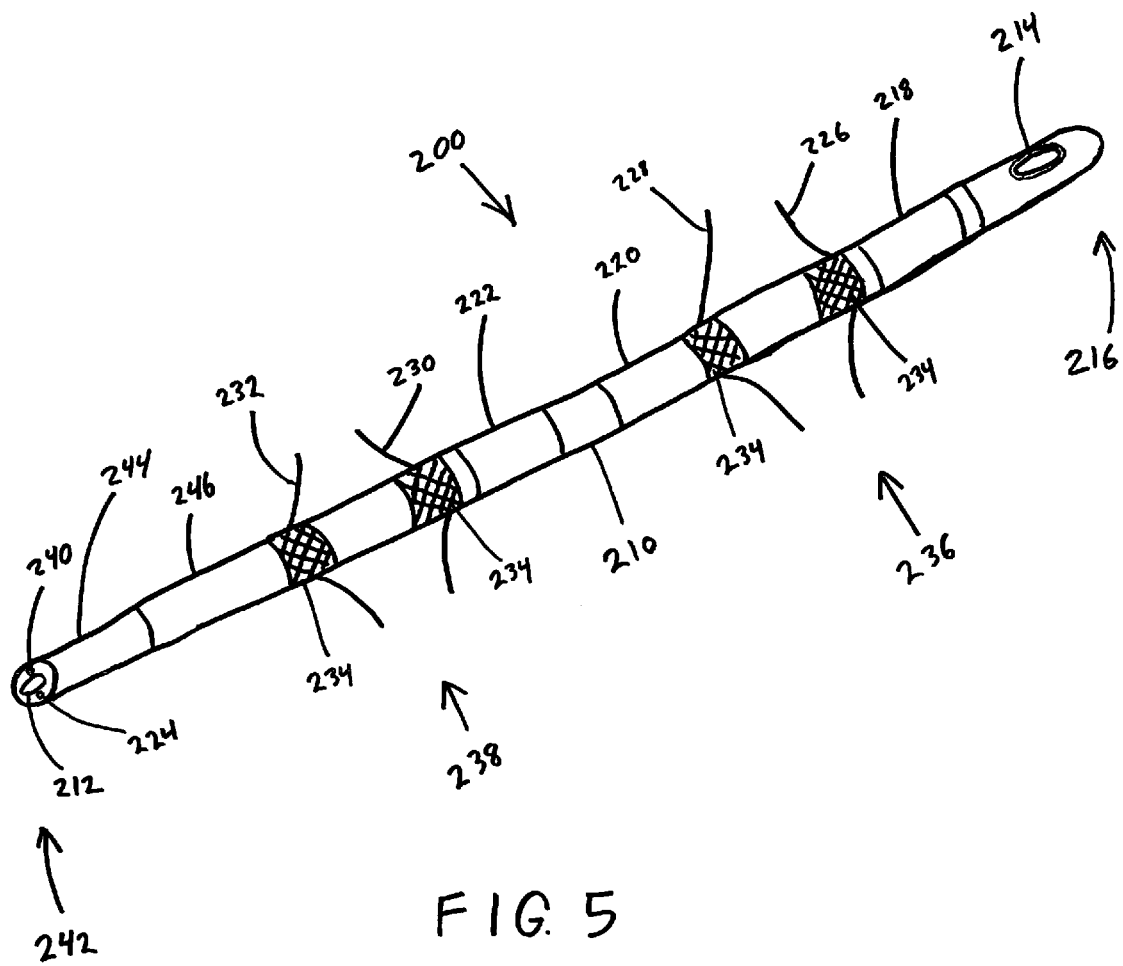
FIG. 5 is a partial cross-sectional, perspective view of an embodiment of an anastomosis device of the present invention.

Referring now to FIG. 5, an embodiment of an anastomosis device of the present invention is not only equipped to enable the radical prostatectomy and urethral anastomosis procedures discussed previously but includes additional feature allowing the same device to be used in procedures including ureteral anastomosis, cystectomy, cystoprostatectomy, and ilio-orthotopic neobladder procedures.

FIG. 5 illustrates a perspective cross-sectional view of the distal end of an anastomosis device 200. The device 200 generally includes an elongate body 210 that contains a central lumen 212 in communication with drainage apertures 214 located at the distal end 216 of the device 200. Also located along the length of the device 200 are a plurality of balloon members including a distal balloon 218, a medial balloon 220, and a proximal balloon 222. One or more of these balloons may be inflated after insertion into the bladder by a flow of fluid through one or more inflation lumens 224.

Also, located on the device 200 are four sets of tines 226, 228, 230 and 232 for holding tissue in place. Each of these sets of tines extends from mesh portions 234. The two distalmost sets of tines 226 and 228 constitute a first pair of tines 236 and the two proximalmost sets of tines 230 and 232 constitute second pair of tines 238. Each of the sets of tines may be actuated by a wire extending through one or more actuating lumens 240. The lumens of the device and shaft 244 extend from the site of the tines to a proximal end 242 of the device 200. The shaft 244 shown in FIG. 5 is representative of only a small segment of the entire shaft length that extends from a connective sheath 246 to a location external to the patient's body.

The anastomosis device 200 of FIG. 5 can be used in radical prostatectomy procedures or uretheral anastomosis procedures by utilizing the distal balloon 218 and tines 226 and 228 rather than balloon 26 and tines 33 and 35, for example, in the manner described in FIGS. 1-4a and their corresponding discussion. The additional tines and balloons of anastomosis device 200 shown in FIG. 5 would remain undeployed or unused in such procedures. In this way, the anastomosis device 200 shown in FIG. 5 is capable of carrying out previously disclosed procedures as well as further procedures that will be discussed in the following.

One procedure in which the anastomosis device 200 of FIG. 5 is especially advantageous is a ureteral anastomosis procedure. A ureteral anastomosis procedure can comprise a ureter-to-ureter procedure as illustrated in FIGS. 6a-d or a ureter-to-bladder procedure as shown in FIGS. 7a-d.

Figure 6B:
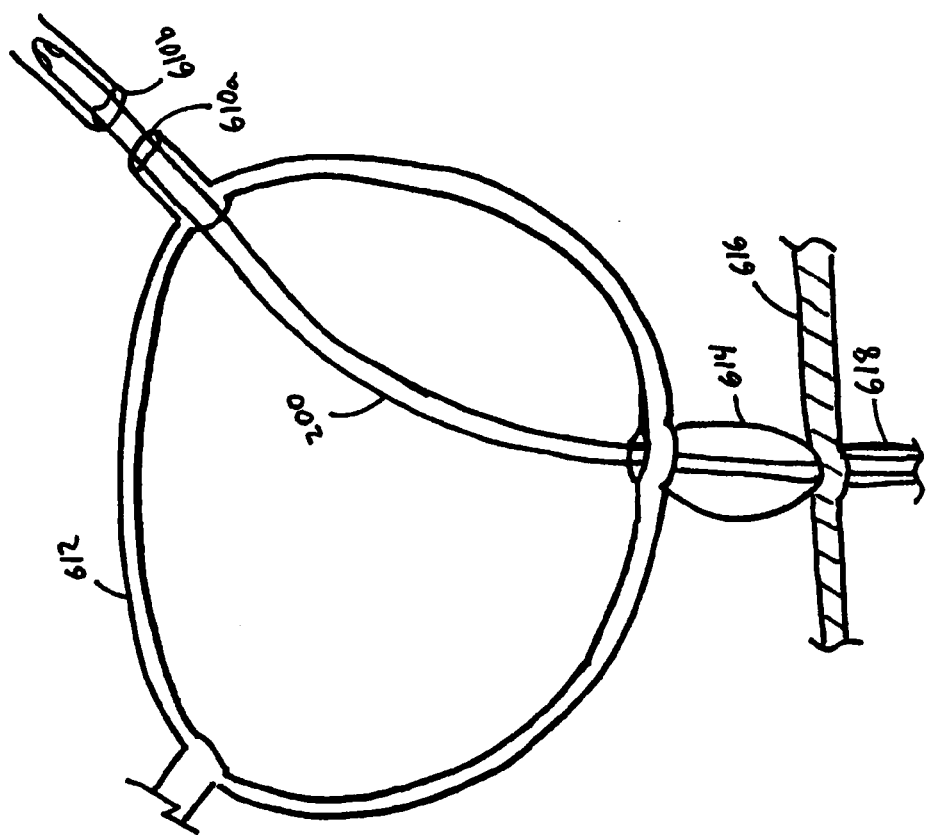
FIG. 6b is a partial cross-sectional view of the anastomosis device of FIG. 5 performing a ureter-to-ureter repair procedure.
Figure 6A:
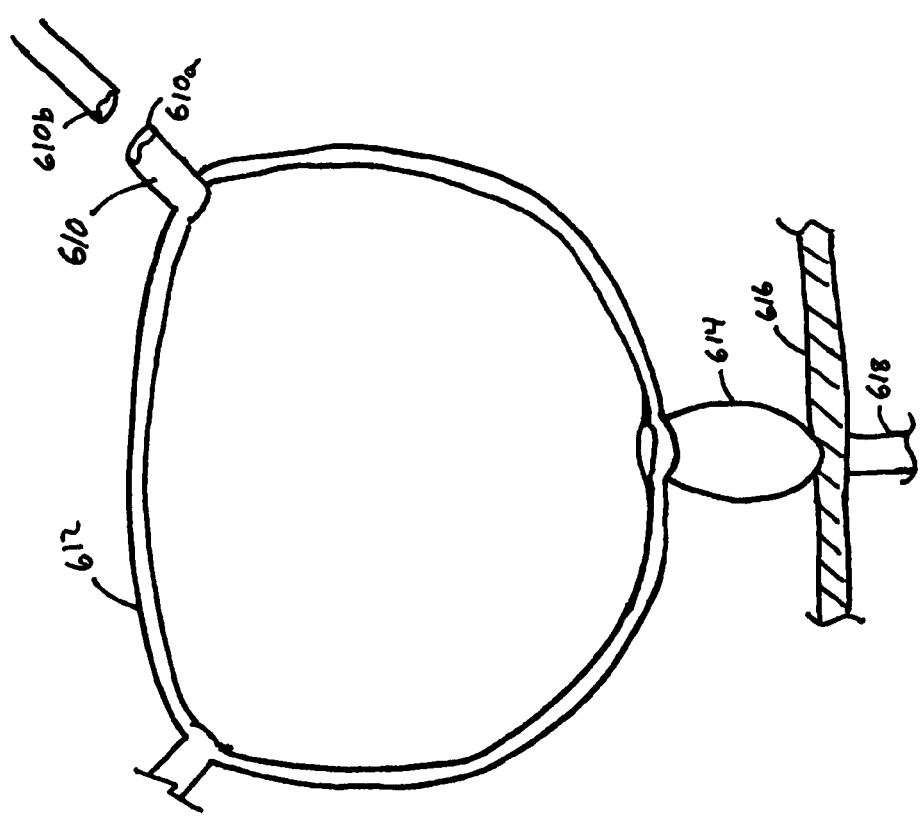
FIG. 6a is a partial cross-sectional view of the anastomosis device of FIG. 5 performing a ureter-to-ureter repair procedure.

In a ureter-to-ureter anastomosis procedure, one of the ureters that extends between the bladder and the kidneys has been cut along its length leaving two severed ureteral portions that must be rejoined together as depicted in FIG. 6a. With reference to FIG. 6a, a ureter-to-ureter anastomosis procedure has taken place leaving a severed ureter 610 with a first severed end 610a and a second severed end 610b. For reference, FIG. 6a also depicts a disconnected bladder 612, prostate 614, perineal floor 616, and urethra 618.

Figure 6D:
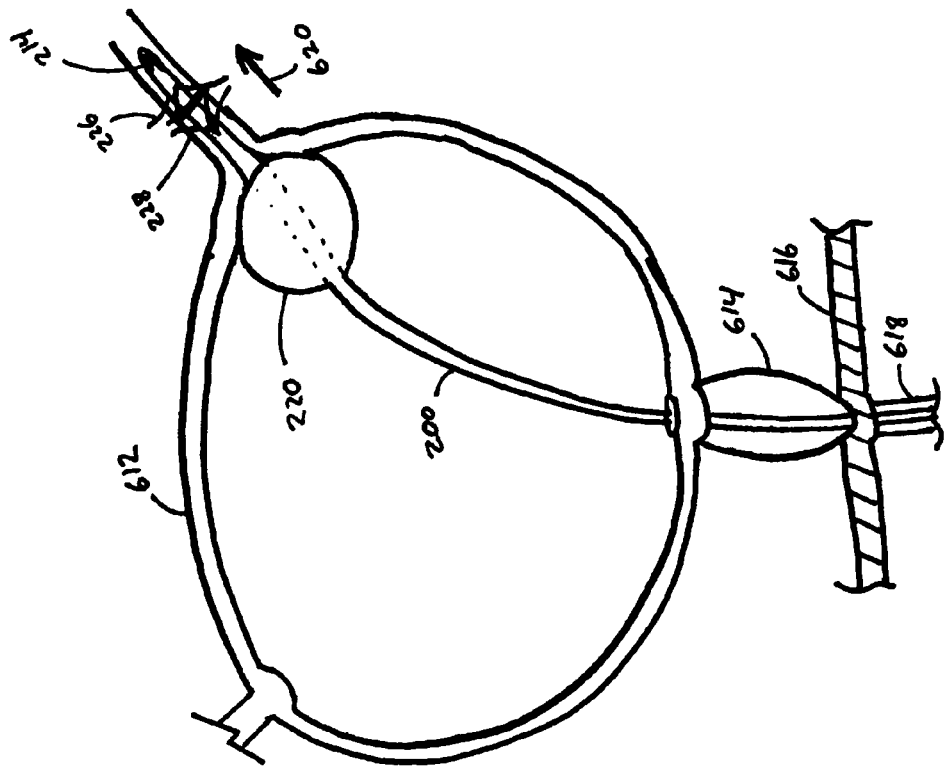
FIG. 6d is a partial cross-sectional view of the anastomosis device of FIG. 5 performing a ureter-to-ureter repair procedure.
Figure 6C:
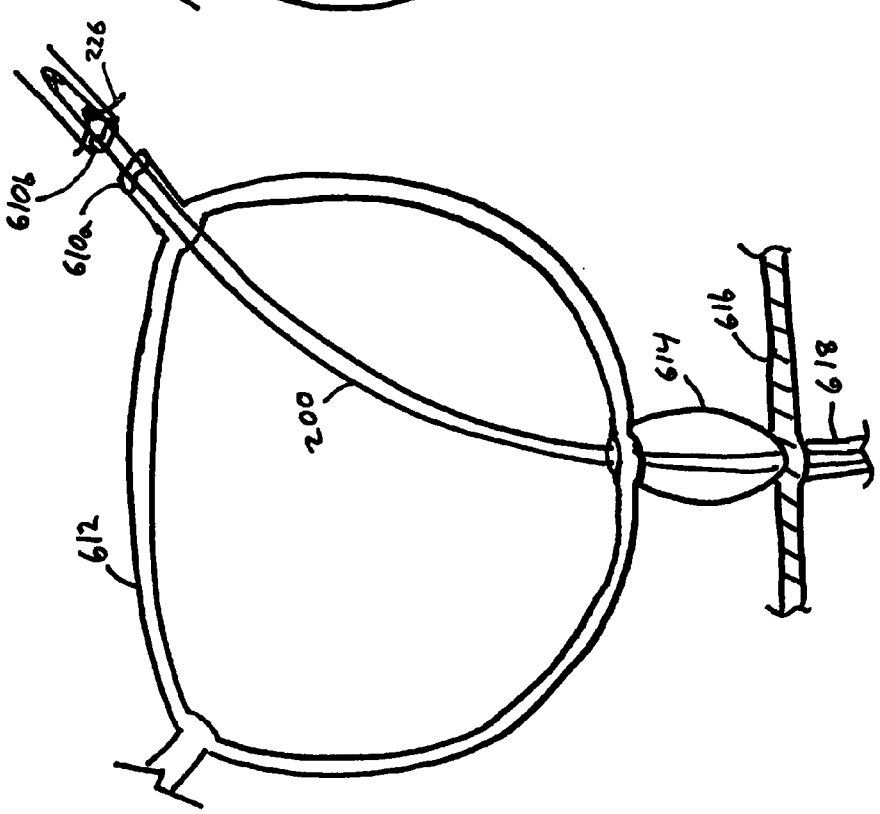
FIG. 6c is a partial cross-sectional view of the anastomosis device of FIG. 5 performing a ureter-to-ureter repair procedure.

To repair the severed ureter-to-ureter connection, the anastomosis device 200 is inserted through the urethra 618, prostate 614, bladder 612 and ureter 610 such that the location of the undeployed distal tines 226 of the device have exited the first severed end 610a of the ureter 610 and are aligned within the second severed end 610b of the ureter 610 as shown in FIG. 6b. As set forth in FIG. 6c, the tines 226 are then deployed to engage the second severed end 610b of the ureter 610 by manipulation of an actuating mechanism inserted through actuating lumen 240. Next, medial balloon 220 is inflated within the bladder as shown in FIG. 6d. Inflating medial balloon 220 serves to urge the bladder 612 and first severed ureteral end 610a toward the second severed ureteral end 610b in direction 620 so they are joined together. Next, the tines 228 are deployed to engage the first severed end 610a through manipulation of a wire passing through an actuating lumen 240. Accordingly, when installed, tines 226 and 228 hold opposing portions of the severed ureter 610 together and in contact with one another for healing. Moreover, the installed anastomosis device 200 utilizes the drainage apertures 214 and lumen 212 to drain urine or fluid from the body. The anastomosis device 200 can be left installed during the healing period and the open drainage lumen allows effective passage of bodily materials without clogging.

In a ureter-to-bladder ansastomosis procedure, the ureter is severed from the bladder. A ureteral stump remains and a severed bladder neck remains which both must be rejoined with one another and repaired. The ureter-to-bladder procedure is illustrated in FIGS. 7a-7d and is operationally similar to the ureter-to-ureter procedure previously described and shown in FIGS. 6a-6d.

FIG. 7a shows a ureter 610 with a severed end 610c that has been detached from connection with the bladder 612. The bladder 612 is left with a bladder neck 622 and a severed tissue surface 624 opposing the end 610c of the removed ureter 610. To reconnect the ureter 610 and bladder 612 the distal end 216 of the anastomosis device 200 is first inserted through the urethra 618, prostate 614 and bladder 610 and into ureter 610 as shown in FIG. 7b.

Figure 7D:
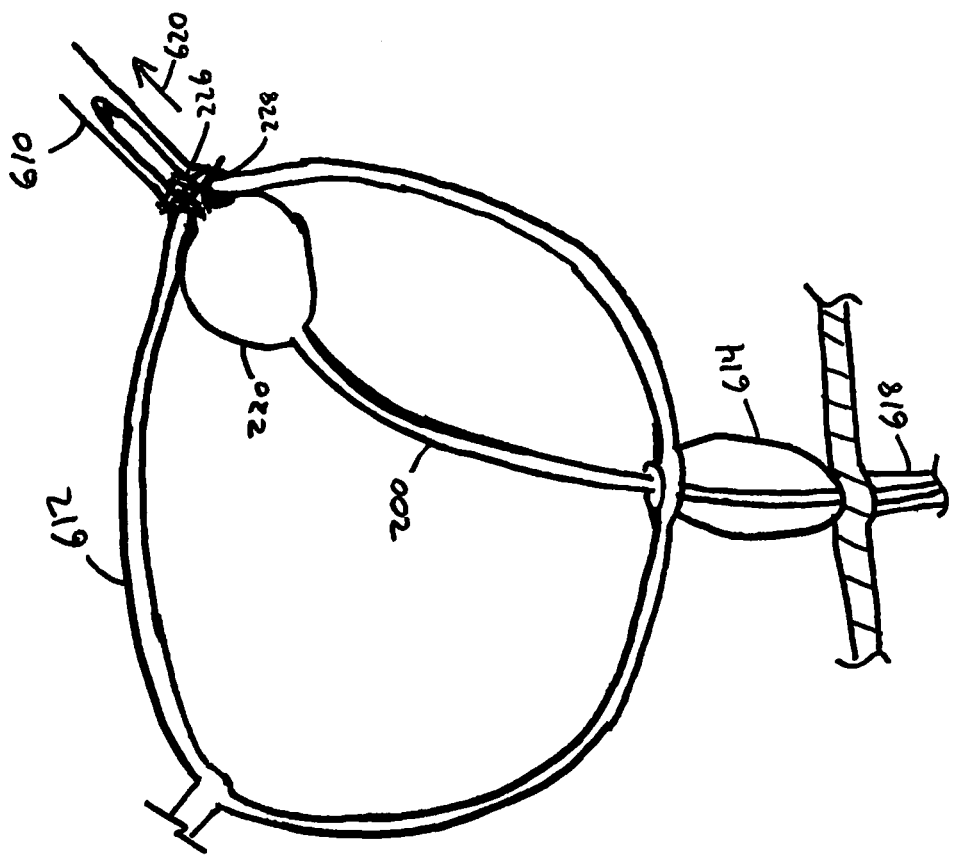
FIG. 7d is a partial cross-sectional view of the anastomosis device of FIG. 5 performing a bladder-to-ureter repair procedure.
Figure 7C:
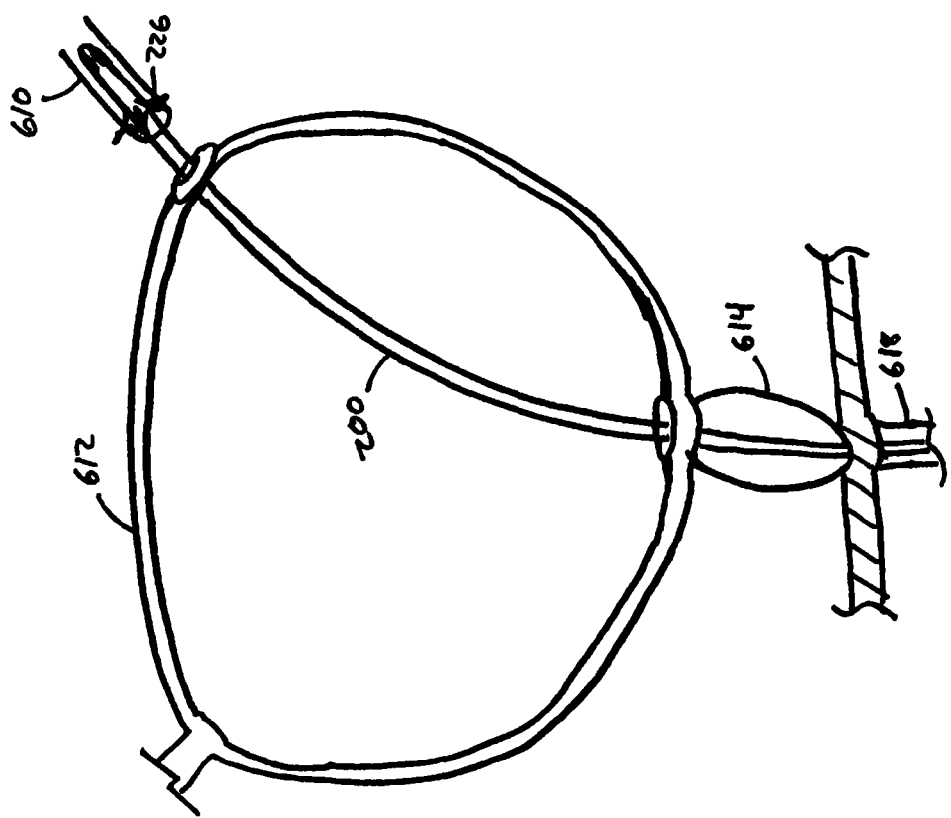
FIG. 7c is a partial cross-sectional view of the anastomosis device of FIG. 5 performing a bladder-to-ureter repair procedure.

Referring now to FIG. 7c, tines 226 can be deployed to engage the severed end 610c of the ureter 610 by operator manipulation of an actuating mechanism inserted through lumen 240. This is followed by inflation of the medial balloon 220 to urge the bladder 612 in direction 620 such that the tissue surface 624 and the end 610c of the ureter 610 are placed together as shown in FIG. 7d. Tines 628 are deployed to engage the bladder neck 622 and to secure the reconnected tissues in place.

In addition to ureteral anastomosis procedures, the anastomosis device 200 can also be used in repairing tissues during cystectomy, cystoprostatectomy and ilio-orthotopic neobladder construction operations. A cystectomy generally involves the surgical removal of all or part of a patient's urinary bladder, often resulting from bladder cancer. Once the bladder has been removed, an ileal conduit is necessary for urinary diversion, or alternatively, some form of replacement bladder is necessary. Similarly, in a cystoprostatectomy the bladder, prostate, and seminal vesicles are removed surgically at the same time. In general, procedures dealing with an ilio-orthotopic neobladder construction involve grafting a new bladder and tissue into the normal position of an original bladder. A neobladder is typically a loop of intestine that is surgically fashioned into a pouch and placed in the location of the original bladder. The neobladder is joined to the urethra and ureters to substitute for the original bladder. Each of these three procedures generally involve replacement of the bladder. Therefore, once the bladder is removed both the severed urethra and severed ureters must be reconnected with a replacement bladder. The anastomosis device 200 shown in FIG. 5 can be used to provide approximated tissue attachments of these members in a similar manner to the ones discusses thus far.

Figure 8B:
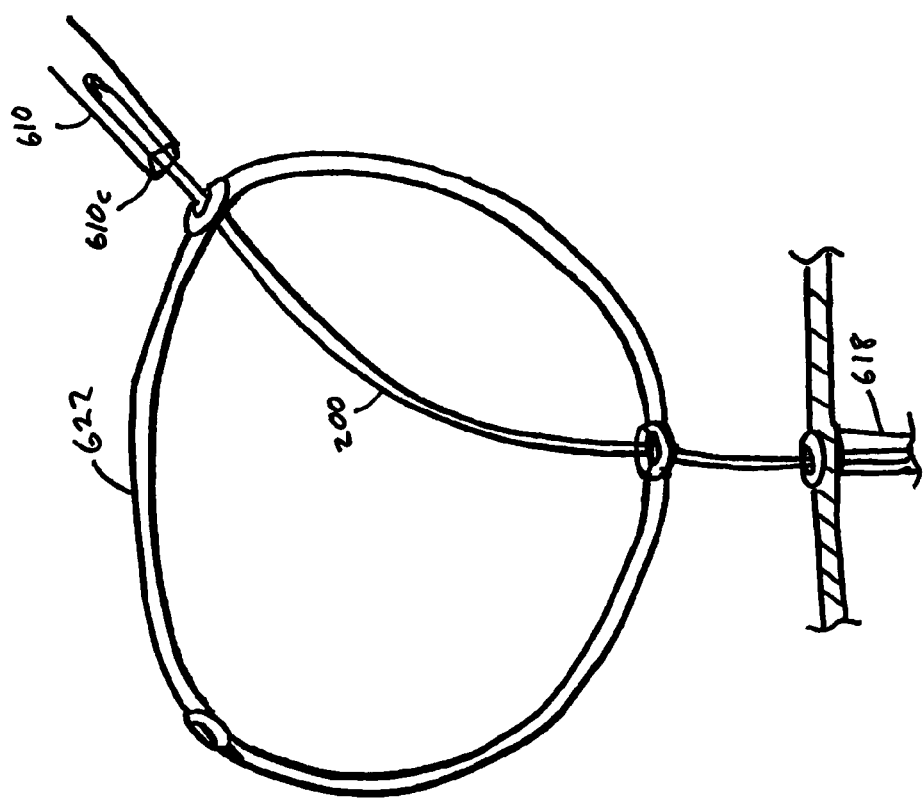
FIG. 8b is a partial cross-sectional view of the anastomosis device of FIG. 5 performing a bladder replacement procedure.
Figure 8A:
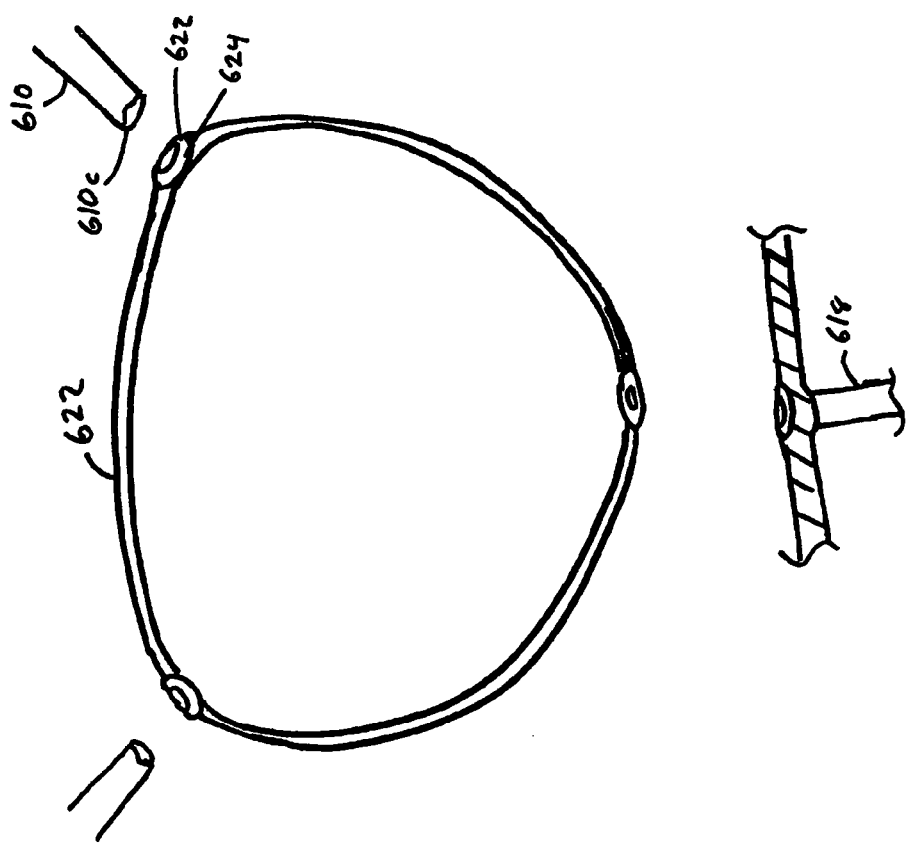
FIG. 8a is a partial cross-sectional view of the anastomosis device of FIG. 5 performing a bladder replacement procedure.
Figure 8D:
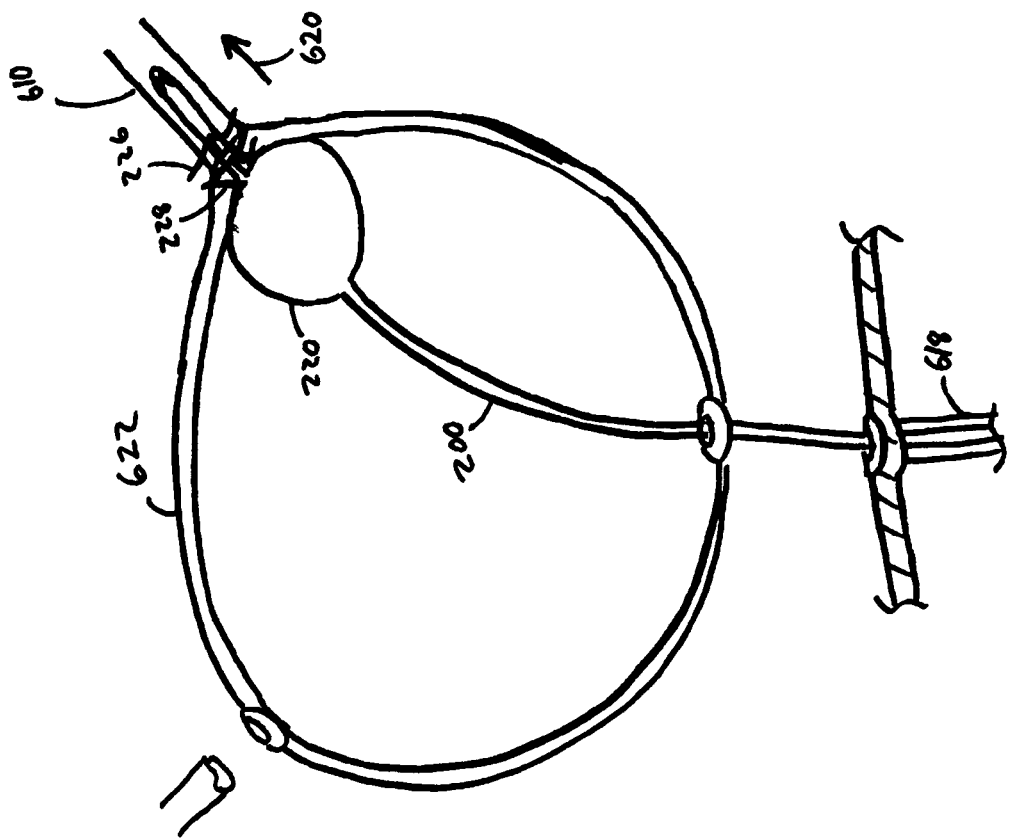
FIG. 8d is a partial cross-sectional view of the anastomosis device of FIG. 5 performing a bladder replacement procedure.
Figure 8C:
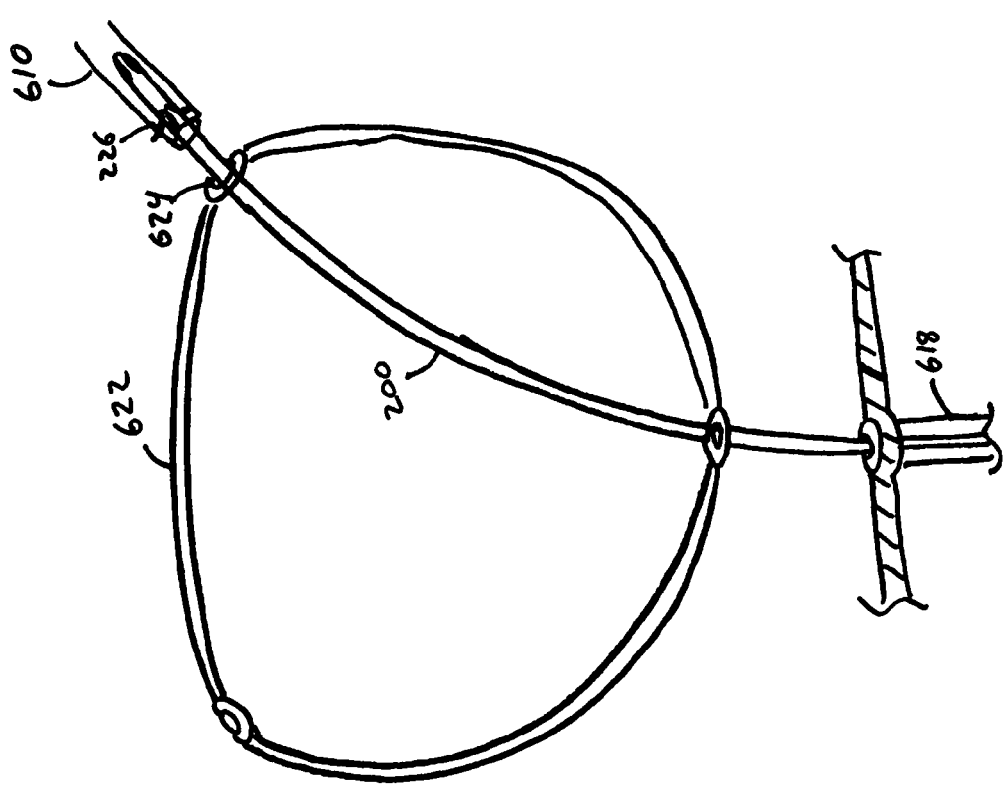
FIG. 8c is a partial cross-sectional view of the anastomosis device of FIG. 5 performing a bladder replacement procedure.

FIGS. 8a-8f disclose a general method for connecting urethra and ureter with a replacement bladder. In a bladder replacement procedure, the urethra 618 and ureter 610 must be rejoined to a separated bladder 622, as shown in FIG. 8a. Once the new bladder member 622 has been replaced in a patient's body, the device 200 is inserted through the urethra 618, new bladder 622, and into a severed ureter 610 such that the distal end 216 of the device is located within the severed ureter wall near end 610c as shown in FIG. 8b. Tines 226 are then deployed to engage the severed ureter 610 by manipulation of an actuating mechanism inserted through actuating lumen 240 as seen in FIG. 8c. Next, medial balloon 220 is inflated in the replacement bladder as shown in FIG. 8d. Medial balloon 220 is inflated by forcing a fluid through the inflation lumen 224. Inflation of the balloon 220 causes the bladder 622 to urge itself toward the severed ureter 610 in the direction 620 until the bladder neck 622 and ureter end 610c are joined. Tines 228 may be deployed within the replacement bladder 622 around neck 628 for support.

Figure 8F:
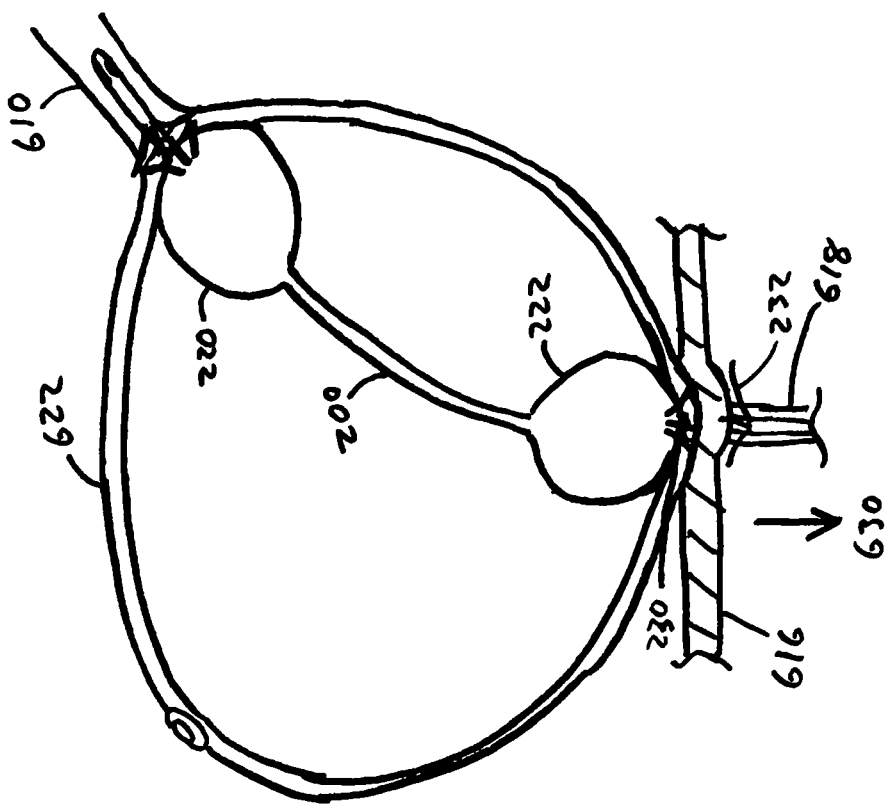
FIG. 8f is a partial cross-sectional view of the anastomosis device of FIG. 5 performing a bladder replacement procedure.
Figure 8E:
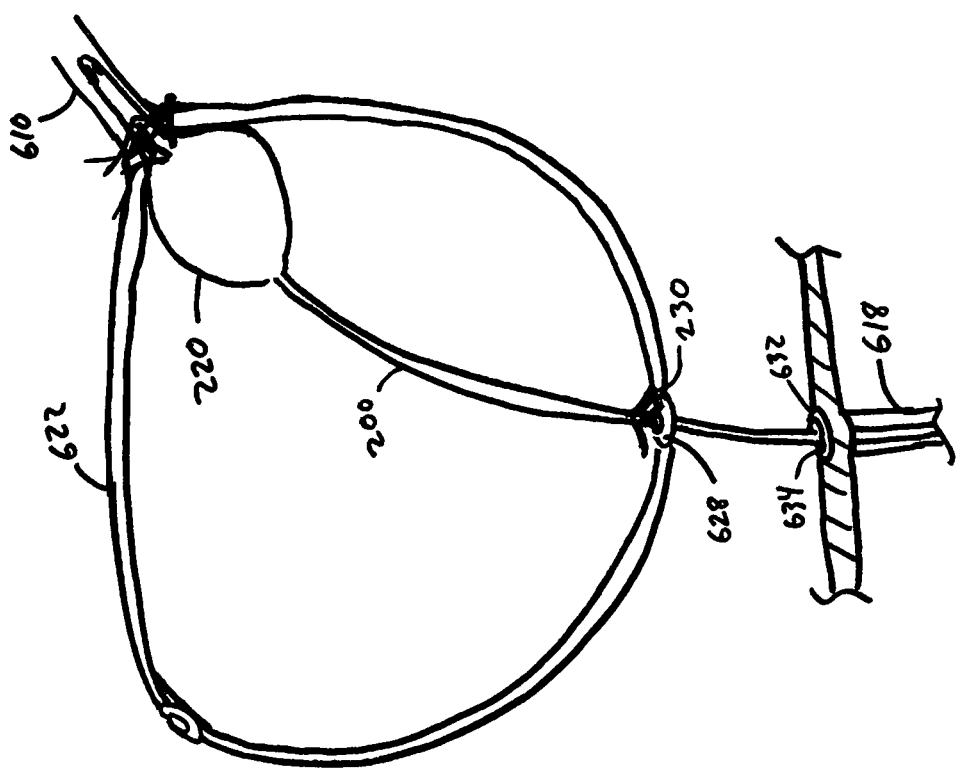
FIG. 8e is a partial cross-sectional view of the anastomosis device of FIG. 5 performing a bladder replacement procedure.

Next, the urethra 618 is attached with the bladder 622 by first engaging tines 230 around the bladder neck 628. The tines 230 are deployed to engage the bladder neck 628 using a wire running through an actuating lumen 240 as shown in FIG. 8e. The proximal balloon 222 is then inflated within the replacement bladder 622 via an inflation lumen 224 as shown in FIG. 8f. Inflation of the proximal balloon 222 combined with manipulation by the surgeon urges the bladder 622 in direction 630 and into engagement with the face 632 of neck 634 of the perineal floor 616 that contains the opening of urethra 618. Tines 232 are then engaged within the urethra 618 to provide additional support for the tissue junction. Therefore, a ureter member and the urethra may be held in place with one another such that healing may occur. The anastomosis device 200 utilizes the drainage apertures 214 and lumen 212 to drain bodily materials during this healing process without clogging.

It should be noted that the device shown in FIG. 5 depicts a single reference 224 for an inflation lumen. While a single lumen may be used for inflation, as described in the previous procedures, use of a plurality of such lumens to separately inflate various inflation balloons should be deemed disclosed herein as well. Likewise, while a single reference is depicted for an actuating lumen 240, this reference is intended to be representative of a plurality of actuating lumens, each equipped with its own wires to control the plurality of various tines necessary for a given procedure.

The methods presented above are meant to illustrate exemplary procedures for particular types of surgery; however, it is understood that similar steps may be used for different surgeries or procedures that may include more, less, or different steps that will be specific to each type of surgery. The steps for the above described surgery, or any other surgeries that use the devices and methods of the present invention, may occur in a different order and may be repeated or omitted, depending on the patient.

Although specific examples have been illustrated and described herein, it will be appreciated by those of ordinary skill in the art that any arrangement calculated to achieve the same purpose could be substituted for the specific example shown. This application is intended to cover adaptations or variations of the present subject matter. Therefore, it is intended that the invention be defined by the attached claims and their legal equivalents.

The invention claimed is:

1. A method for performing a ureter-to-ureter anastomosis procedure comprising:
   providing an anastomosis device including a distalmost pair of tines and a medial inflation balloon, said distalmost pair of tines including a first tine set and a second tine set with each tine set being located between a distal end and the medial inflation balloon;
   advancing the distal end of the anastomosis device such that the distal end leads the anastomosis device through a urinary tract and into a severed ureteral member such that the first tine set is positioned within a distal severed ureter portion and the second tine set is positioned within a proximal severed ureter portion, said proximal severed ureter portion being attached to a bladder;
   extending the first tine set to grasp the distal severed ureter portion;
   inflating the medial inflation balloon within the bladder such that the medial inflation balloon is proximate the proximal severed ureter portion;
   pushing on the bladder with the medial inflation balloon to direct the proximal severed ureter portion into contact with the distal severed ureter portion; and
   extending the second tine set to grasp the proximal severed ureter portion and retain the proximal severed ureter portion and the distal severed ureter portion in approximation.

2. The method of claim 1, further comprising:
   draining fluid in the distal severed ureter portion through a drainage aperture at the distal end of the anastomosis device.

3. The method of claim 1, further comprising
   maintaining approximation of the proximal severed ureter portion and the distal severed ureter portion throughout a healing period.

* * * * *